Figure 1:
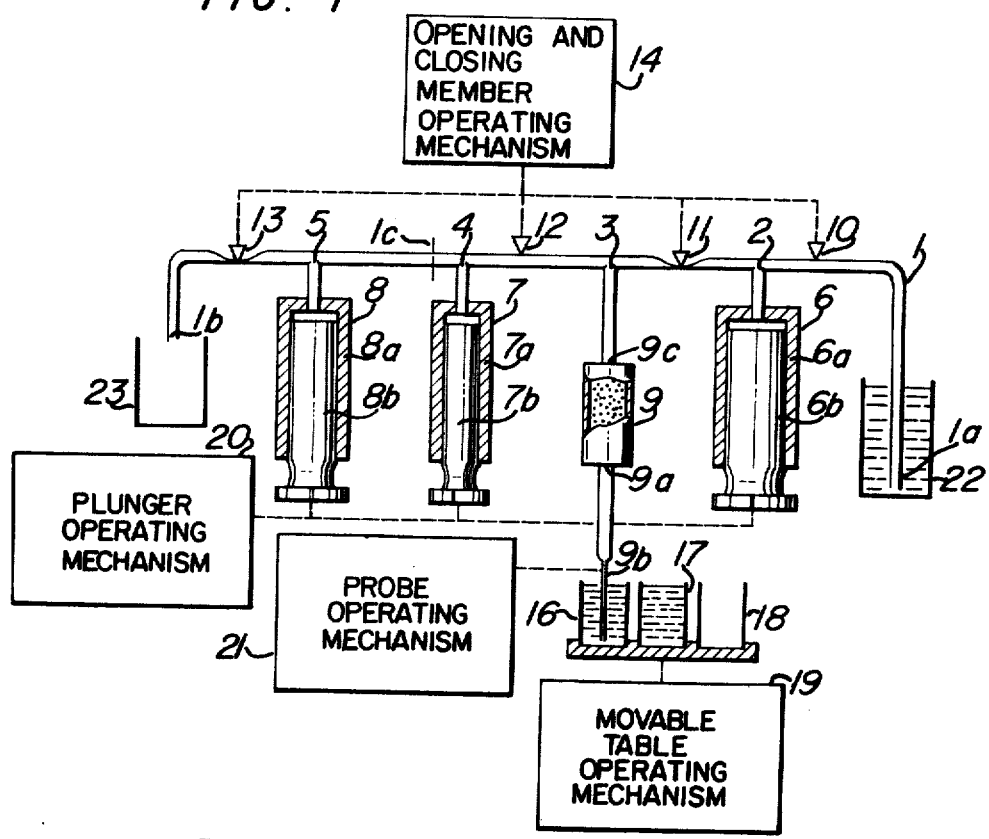

United States Patent
Ozawa

[11] 3,963,614
[45] June 15, 1976

[54] APPARATUS FOR REMOVING UNNECESSARY COMPONENTS FROM SAMPLES

[75] Inventor: Kyoichi Ozawa, Mito, Japan

[73] Assignee: Hitachi, Ltd., Japan

[22] Filed: Nov. 5, 1971

[21] Appl. No.: 195,996

[30] Foreign Application Priority Data
Nov. 9, 1970    Japan............................... 45-97877

[52] U.S. Cl............................................ 210/198 C
[51] Int. Cl.² ........................................ B01D 15/08
[58] Field of Search...... 210/198 A, 198 C, DIG. 23

[56] References Cited
UNITED STATES PATENTS

| | | | |
|---|---|---|---|
| 3,446,057 | 5/1969 | Bakalyar et al.............. | 210/198 C |
| 3,508,880 | 4/1970 | Hrdina........................ | 210/198 C |
| 3,518,874 | 7/1970 | Hrdina........................ | 210/198 C X |
| 3,583,230 | 6/1971 | Patterson..................... | 210/198 C X |
| 3,593,854 | 7/1971 | Swank.......................... | 210/DIG. 23 |
| 3,666,105 | 5/1972 | Fox............................. | 210/198 C |

*Primary Examiner*—John Adee
*Attorney, Agent, or Firm*—Craig & Antonelli

[57] ABSTRACT

A sample is sucked from a probe into a column filled with a porous material and successively thereafter an auxiliary liquid is sucked from the probe and passed through the column, whereby unnecessary components in the sample are moved through the column and the component which it is desired to analyze remains within the column. Then, a discharging liquid is passed through the column and the probe, whereby the desired component in the column is discharged through the probe.

28 Claims, 2 Drawing Figures

APPARATUS FOR REMOVING UNNECESSARY COMPONENTS FROM SAMPLES

This invention relates to an apparatus for removing unnecessary components from samples and more particularly to such an apparatus which is adapted for carrying out the removal of the unnecessary components from a sample within an automatic analyzing apparatus for analyzing a desired component in the sample.

In an automatic analyzing apparatus for analyzing a specific component which it is desired to analyze in samples such, for example, as blood serums, the unnecessary components in the samples, e.g. protein in blood serums, occasionally interfere with the measurement of analysis of the component depending upon the type of sample.

In such a case, it has been conventional to remove the unnecessary components from the sample, before the measurement or analysis by the automatic analyzing apparatus, by adding a reagent to the sample to precipitate the unnecessary components and removing the resultant precipitates by means of centrifugal separation or filtration. However, this method is unsatisfactory in that not only much labor and time are required for the operation of removing the unnecessary components but also there is the chance of error in the identification of samples during repetitive performance of the operation. Thus, it becomes very important to incorporate the operation in the system itself of the automatic analyzing apparatus wherever feasible.

An object of the present invention is to provide an apparatus which is adapted for carrying out the removal of the unnecessary components from a sample within an automatic analyzing apparatus for analyzing a specific component of the sample.

Another object of the invention is to provide an apparatus which is capable of quickly removing the unnecessary components from a sample.

According to the present invention there is provided an apparatus for removing unnecessary components from samples, which comprises a column filled with a porous material which allows the unnecessary components in the sample to pass therethrough but retains the component which it is desired to analyze, a probe connected with one end of said column, means for sucking the sample from said probe into said column, means for sucking an auxiliary liquid from said probe through said column successively after the suction of the sample thereby urging said unnecessary components to pass through said column while retaining the component desired to be analyzed within said column, and means for passing a discharge liquid through said column and said probe to discharge the component desired to be analyzed from said column.

The apparatus of the invention described above completely attain the objects set forth above and simultaneously enables the following advantages to be obtained;

1. Since the component retained within the column which is to be submitted to analysis is discharged therefrom by the discharging liquid, the porous material is automatically washed and cleaned by said discharging liquid and, therefore, the useful life thereof can be prolonged.

2. Since the discharging liquid passes through the probe during discharge of the component to be analyzed from the column, the inner wall of said probe is automatically washed out by said discharging liquid and thereby the contamination of samples by each other can be avoided.

3. In the analysis of a specific component of a given sample by an automatic analyzing apparatus, it is necessary to add a diluent or reactive reagent to the sample. In the apparatus of this invention, this can be automatically achieved by the operation of passing the discharging liquid through the column for discharging the selected component from said column.

Figure 2:
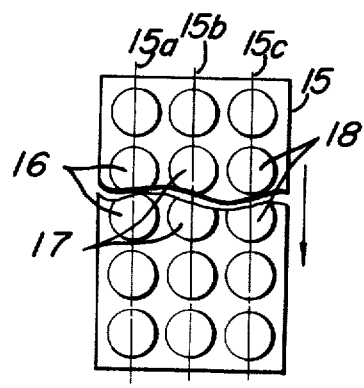

The above and other objects and features of the present invention will become apparent from the following detailed description when taken in conjunction with the accompanying drawings. In the drawings;

FIG. 1 is a schematic illustration of an embodiment of the unnecessary component removing apparatus according to the present invention; and FIG. 2 is a plan view, partially cut away, of the movable table in the apparatus shown in FIG. 1.

Referring to the drawings and particularly to FIG. 1, the apparatus includes a conduit 1 of a limited length which is made of an elastic material and has a first opening 2, a second opening 3, a third opening 4 and a fourth opening 5 formed therein. Pumps 6, 7 and 8 are respectively composed of cylinders 6a, 7a and 8a and pistons or plungers 6b, 7b and 8b slidably received in said respective cylinders. A column 9 is filled with an unnecessary component removing material and has one end of a probe 9b connected with one end 9a thereof by means of an elastic tube. As the material to be packed in the column 9, porous materials such as Zeolite (trade name), polystyrene resin, porous galactomannan, hardened rubber, agar gel, polyacrylamide gel, porous dextran gel (Sephadix in trade name) and agarose gel made from agar are used. The sucking and discharging end of the pump 6, the other end 9c of the column 9, and the sucking and discharging ends of the pumps 7 and 8 are connected with the first opening 2, the second opening 3, the third opening 4 and the fourth opening 5 of the conduit 1 respectively. Passage opening and closing members 10, 11, 12 and 13 are respectively provided at an optional location between the first opening 2 and one end 1a of the conduit 1, between the first opening 2 and the second opening 3, between the second opening 3 and the third opening 4, and between the fourth opening 5 and the other end 1b of the conduit 1, respectively, to open or close said conduit 1 at their locations. These passage opening and closing members 10, 11, 12 and 13 are operated by an opening and closing member operating mechanism 14 in such a manner that the passage in the conduit 1 is opened or closed by the opening and closing members 10 and 12 at the location of said members and opened or closed by the opening and closing members 11 and 13 at the locations of said members alternately automatically. A movable table 15 carries thereon a plurality of sample containers 16, a plurality of auxiliary liquid containers 17 and a plurality of sample receiving receptacles 18, which are respectively arranged in three rows 15a, 15b and 15c in evenly spaced relation to each other as shown in FIG. 2. This table 15 is moved by a movable table operating mechanism 19 intermittently in a stop and go fashion one step or one pitch in the direction of the arrow (in a direction normal to the sheet of FIG. 1) upon completion of each of the alternate passage opening and closing operations of the opening and closing members 10 and 12, and 11 and 13. A plunger operating mechanism 20 operates the plungers 6b, 7b and 8b of the respective pumps 6, 7 and 8 in such a sequence that the plungers 6b and 7b are first pulled down while the conduit 1 is being opened by the opening and closing members 10 and 12 at their locations and then the plunger 8b is pulled down while the conduit 1 is being opened by the opening and closing members 10 and 12 at their locations, and thereafter the plungers 6b, 7b and 8b are concurrently pushed up after the conduit 1 is opened by the opening and closing members 11 and 13 at their locations. Namely, the plunger operating mechanism 20 causes the pumps 6 and 7 to suck liquids while the conduit 1 is being closed by the opening and closing members 11 and 13 at their locations and then causes the pump 8 to suck the liquid while the conduit 1 is closed by the opening and closing members 11 and 13 at their locations, and thereafter causes the pumps 6, 7 and 8 to discharge the sucked liquids concurrently after the conduit 1 is closed by the opening and closing members 10 and 12 at their locations. The probe 9b is operated by a probe operating mechanism 21 in such a manner that it is held submerged at its lower end into a sample contained in the sample container 16 during the liquid sucking operations of the pumps 6 and 7, is held submerged into an auxiliary liquid contained in the auxiliary liquid container 17 during the sucking operation of the pump 8 and is transferred into the sample receiving receptacle 18 during the liquid discharge operations of the pumps 6, 7 and 8. The end 1a of the conduit 1 is submerged into a washing liquid contained in a container 22, and the other end 1b thereof is located above an unnecessary component receptacle 23. The washing liquid container in the container 22 may be substituted by a reactive reagent or diluent, and the auxiliary liquid contained in the container 17 may be a washing liquid or diluent but must not be the same as the sample contained in the container 16.

The apparatus shown in FIG. 1 of the present invention constructed as described above operates in the following manner:

The sample container 16 is filled with a sample, e.g. blood serum, the auxiliary liquid container 17 with an auxiliary liquid, e.g. a diluent or washing liquid and the washing liquid container 22 with a washing liquid, diluent or reactive reagent.

Now, let it be supposed that the conduit 1 is opened by the opening and closing members 10 and 12 at their locations and closed by the opening and closing members 11 and 13 at their locations, and further that the movable table 15 is held stationary; the plungers 6b, 7b and 8b are at the ends of their upward strokes; and the probe 9b has its lower end submerged into the sample in any one of the sample containers 16.

When the plungers 6b and 7b are pulled down under such condition by the plunger operating mechanism 20, the washing liquid, diluent or reactive reagent in the container 22 is sucked into the cylinder 6a from the end 1a of the conduit 1 and at the same time, the sample in the container 16 is sucked in a predetermined quantity into the column 9 through the probe 9b. In this case, the sucking operation by the plunger 7b is effected to such an extent that the container 16 will not be emptied.

Then, the probe 9b is transferred from the container 16 to the container 17 by the probe operating mechanism 21 and dipped into the auxiliary liquid such as a washing liquid or diluent therein. In this state, the plunger 8b is pulled down by the plunger operating mechanism 20, whereby the washing liquid or diluent is the container 17 is sucked into the cylinder 8a through the probe 9b and the column 9, following the sample previously sucked into said probe. Where the sample is blood serum, the high molecular weight protein present therein which is the unnecessary component passes through the column 9 and other low molecular weight component which it is desired to analyze is retained within the column 9. In other words, the unnecessary components such as protein and the other component which it is desired to analyze are separated from each other by virtue of the molecular weight differential by means of the porous material constituting an unnecessary compound removing agent and packed in the column 9, and the unnecessary components pass through the column 9 and the component to be analyzed remains within said column.

Then, the passage opening and closing members 10 and 12 are operated by the opening and closing member operating mechanism 14 to close the passage in the conduit 1 at their locations and the passage opening and closing members 11 and 13 are concurrently operated by said mechanism 14 to open the passage at their locations. Further, the probe 9b is shifted from the container 17 to the receptacle 18 by the action of the probe operating mechanism 21.

In this state, the plungers 6b, 7b and 8b are concurrently pushed up by the plunger operating mechanism 20, so that the component to be analyzed which is retained in the column 9 is urged by the diluent, washing liquid or reactive reagent to move outwardly of said column and discharged into the receptacle 18 through the probe 9b. At the same time, the unnecessary components in the cylinder 8a are discharged into the receptacle 23 through the other end 1b of the conduit 1. If liquid is present in the cylinder 7a, this liquid will also be discharged into the receptacle 23 through the other end 1b of the conduit 1.

Upon completion of the above operation, the movable table 15 is moved one step in the direction of the arrow (FIG. 2) by the movable table operating mechanism 19. Thereafter, the same operation as above described will be repeated.

If the column 9, the containers 17 and 23, the pump 8 and the passage opening and closing member 13 are removed from the apparatus and the conduit 1 is sealed at the point 1c, the resultant apparatus can be used to perform the following operation: Namely, when the plungers 6b and 7b are pulled down under the condition that the conduit 1 is closed at the location of the opening and closing member 11 by said member and opened at the locations of the opening and closing members 10 and 12 by said members, the liquid in the container 22 is sucked into the cylinder 6a and at the same time the sample contained in the container 16 is sucked into the probe 9b. Thereafter, the opening and closing members 10 and 12 are operated to close the conduit 1 at their locations and the opening and closing member 11 is operated to open the conduit 1 at its location, and further the probe 9b is transferred into the container 18. Thereafter, the plungers 6b and 7b are concurrently pushed up, whereby the sample previously sucked into the probe 9b is discharged into the container 18 and the liquid (diluent, washing liquid or reactive reagent) previously sucked into the cylinder 6a is also discharged into said container 18 following said sample while washing out the inner wall of the probe 9b. Such an apparatus is well known as pipetter or diluter which constitutes a part of an automatic analyzing apparatus. The apparatus of the invention shown in FIG. 1 is one which performs the unnecessary component removing operation while retaining the inherent function of the above-described apparatus. Therefore, it will be understood that the apparatus shown in FIG. 1 is the most suitable one for removing the unnecessary components within an automatic analyzing apparatus which is designed to continuously analyze a large number of samples.

It will also be understood that by employing the apparatus of FIG. 1, the removal of unnecessary components can be achieved quickly because, in the apparatus, the removal of unnecessary components is effected by forced suction and discharge operations.

Further, in the apparatus of FIG. 1 the washing of the inner wall of the probe is achieved substantially and the washing of the porous material within the column is achieved also automatically. Therefore, it will be appreciated that the contamination of samples by each other can be avoided and the useful life of the porous material can be extended.

In the apparatus of FIG. 1, when the auxiliary liquid is not sucked through the probe successively after the suction of the sample through said probe, air must be sucked through the probe and column at the time of suction of the sample, because otherwise the sample remains in the probe and the column with the unnecessary components present therein, which will be discharged into the container 18 through said probe by the following discharge operation, and thus the removal of the unnecessary components will not substantially be achieved. If air is sucked into the probe and column, however, the removal of the unnecessary components cannot effectively be carried out. The apparatus of FIG. 1 is free of such problem since the auxiliary liquid is sucked following the suction of the sample and hence no air is substantially sucked through the probe.

It will be obvious that in the apparatus of FIG. 1 the sucking and discharging effects of the pump 8 can be obtained by the pump 7 and, therefore, the pump 8 can be eliminated from the apparatus.

The passage opening and closing member operating mechanism, the plunger operating mechanism, the probe operating mechanism and the movable table operating mechanism shown in FIG. 1 may be essentially of the types well known in the art and hence will not be described in detail herein.

Although the present invention has been described and illustrated herein in terms of a specific embodiment thereof, it should be understood that the apparatus shown in FIGS. 1 and 2 is merely an embodiment to assist in understanding of the invention and many changes and modifications are possible without deviating the spirit of the invention.

What is claimed is:

1. An apparatus for removing unnecessary components from samples, comprising a column filled with a porous material which allows the unnecessary components in a sample to pass therethrough but retains a component which it is desired to analyze, a probe connected with one end of said column, means for sucking the sample through said probe into said column, means for sucking an auxiliary liquid through said probe and said column successively after the suction of the sample thereby urging the unnecessary components to pass through the column while retaining the component desired to be analyzed within said column, and means for passing a discharging liquid through said column and said probe to discharge the component desired to be analyzed from said column.

2. An apparatus as defined in claim 1, wherein there is provided means for discharging the unnecessary components passing through the column into a receptacle.

3. An apparatus as defined in claim 2, wherein said auxiliary liquid consists of one of a washing liquid and a diluent and said discharging liquid consists of one of a washing liquid, a diluent and a reactive reagent.

4. An apparatus for removing unnecessary components from samples, comprising a column filled with a porous material which retains a low molecular weight component of a sample which it is desired to analyze but allows unnecessary high molecular weight components of the sample to pass therethrough, a probe connected with one end of said column, means for sucking the sample through said probe into said column, means for sucking an auxiliary liquid through said probe and said column successively after the suction of the sample thereby urging the unnecessary components to pass through the column while retaining the component desired to be analyzed within said column, and means for passing a discharging liquid through said column and said probe in a direction opposite to the sample sucking direction.

5. An apparatus as defined in claim 4, wherein there is provided means for discharging the unnecessary components passing through the column into a receptacle and said auxiliary liquid consists of one of a washing liquid and a diluent; said discharging liquid consists of one of a washing liquid, a diluent and a reactive reagent; and said porous material consists of one of Zeolite, polystyrene resin, porous galactomannan, hardened rubber, agar gel, polyacrylamide gel, porous dextran gel and agarose gel made from agar.

6. An apparatus for removing unnecessary components from samples, comprising a column filled with a porous material which retains a low molecular weight component of a sample which it is desired to analyze but allows unnecessary high molecular weight components of the sample to pass therethrough; a probe connected with one end of said column; first and second pump means for effecting suction and discharge of liquid; an elastic conduit of a limited length provided with first, second and third openings arranged intermediate the ends thereof, said first pump means being connected to said first opening, the other end of said column being connected with said second opening, said second pump means being connected with said third opening; first, second, third and fourth passage opening and closing members provided between said one end of said conduit and said first opening, between said first opening and said second opening, between said second opening and said third opening and between said third opening and said the other end of said conduit, respectively, for opening or closing the passage in said conduit at their locations; means for operating said respective passage opening and closing members in such a manner that said conduit is opened or closed by said first and third passage opening and closing members at their locations and said conduit is opened or closed by said second and fourth passage opening and closing members at their locations alternately; and means for operating said first and second pump means to controllably shift the position of the apparatus from a first stage in which said first and second pump means perform a sucking operation while said conduit is being opened by said first and third passage opening and closing members at their locations, to a second stage in which said second pump means only performs a sucking operation under the same condition of the conduit as above described and thence to a third stage in which said first and second pump means perform a discharging operation while said conduit is being closed by said first and third passage opening and closing members at their locations, in said first stage said first pump means sucking a discharging liquid from said one end of said conduit thereinto and said second pump means sucking the sample through said probe into said column, in said second stage said second pump means sucking an auxiliary liquid through said probe and said column successively after the suction of the sample thereby urging the unnecessary components to pass through said column while retaining the component desired to be analyzed within said column, and in said third stage discharging liquid previously sucked in said first pump means being discharged through said column and said probe together with the component desired to be analyzed and said unnecessary components previously sucked in said second pump means being discharged from the other end of said conduit.

7. An apparatus as defined in claim 6, wherein there are provided a container for containing the sample, a container for containing the auxiliary liquid, a container for receiving the discharging liquid containing the component desired to be analyzed and discharged through said probe, and means for operating said probe in such a manner that it is dipped into the sample in said sample container in said first stage, is shifted into said auxiliary liquid container and dipped into the auxiliary liquid therein in said second stage and is shifted into said discharging liquid receiving container in said third stage.

8. An apparatus as defined in claim 7, wherein there are provided a movable table carrying thereon a plurality of said sample containers, a plurality of said auxiliary liquid containers and a plurality of said discharging liquid receiving containers which are arranged in three rows respectively in evenly spaced relation to each other, and means for intermittently moving said movable table a predetermined distance upon completion of each of said first, second and third stages.

9. An apparatus as defined in claim 8, wherein said auxiliary liquid consists of one of a washing liquid and a diluent, and said discharging liquid consists of one of a washing liquid, a diluent and a reactive reagent.

10. An apparatus as defined in claim 9, wherein said porous material consists of one of Zeolite, polystyrene resin, porous galactomannan, hardened rubber, agar gel, polyacrylamide gel, porous dextran gel and agarose gel made from agar.

11. An apparatus as defined in claim 7, wherein there are provided a movable table carrying thereon at least one auxiliary liquid container, in addition to a plurality of said sample containers and a plurality of said discharging liquid receiving containers which are arranged in two rows respectively in evenly spaced relationship to one another, and means for intermittently moving said movable table a predetermined distance upon completion of each of said first, second and third stages.

12. Apparatus for separating undesired components from a fluid sample comprising:

sample holding means for holding a fluid sample containing both undesired and predetermined desired components, auxiliary liquid holding means for holding a supply of auxiliary liquid separate from said fluid sample, discharging liquid holding means for holding a supply of discharging liquid separate from said fluid sample, a column filled with a porous material which includes means for permitting passage of said undesired sample components through said column while retaining said desired sample components in said column, first pumping means for pumping portions of said fluid sample from said sample holding means in a first direction through said column, second pumping means for pumping portions of said auxiliary liquid from said auxiliary liquid holding means in said first direction through said column, third pumping means for pumping portions of said discharging liquid from said discharging liquid holding means in a second direction, opposite said first direction, through said column, and pumping control means for controlling sequential operation of said pumping means such that: said first pumping means first pumps portions of said fluid sample in said first direction through said column, said second pumping means then pumps said auxiliary liquid through said column in said first direction to assist in forcing said undesired components through and away from said column, and said third pumping means then pumps said discharging liquid through said column in said second direction to discharge the desired components retained in said column after operation of said first and second pumping means.

13. Apparatus according to claim 12, wherein means are provided for preventing communication of said column with said discharging liquid holding means when said first pumping means is pumping portions of said fluid sample in said first direction through said column.

14. Apparatus according to claim 12, wherein means are provided for preventing communication of said column with said discharging liquid holding means when said second pumping means is pumping auxiliary liquid in said first direction through said column.

15. Apparatus according to claim 13, wherein means are provided for preventing communication of said column with said discharging liquid holding means when said second pumping means is pumping auxiliary liquid in said first direction through said column.

16. Apparatus according to claim 12, further comprising undesired component receptacle means separate from each of said holding means for accepting the undesired components and auxiliary liquid pumped by said second pumping means in said first direction through said column.

17. Apparatus according to claim 16, wherein means are provided for preventing communication of said undesired component receptacle means with said first pumping means and said column when said first pumping means is pumping portions of said fluid sample in said first direction through said column.

18. Apparatus according to claim 16, wherein means are provided for preventing communication of said undesired component receptacle means with said column when said third pumping means is pumping said discharging liquid through said column in said second direction.

19. Apparatus according to claim 17, wherein means are provided for preventing communication of said undesired component receptacle means with said column when said third pumping means is pumping said discharging liquid through said column in said second direction.

20. Apparatus according to claim 15, further comprising undesired component receptacle means separate from each of said holding means for accepting the undesired components and auxiliary liquid pumped by said second pumping means in said first direction through said column.

21. Apparatus according to claim 20, wherein means are provided for preventing communication of said undesired component receptacle means with said first pumping means and said column when said first pumping means is pumping portions of said fluid sample in said first direction through said column.

22. Apparatus according to claim 21, wherein means are provided for preventing communication of said undesired component receptacle means with said column when said third pumping means is pumping said discharging liquid through said column in said second direction.

23. Apparatus according to claim 12, further comprising sample receiving receptacle means separate from each of said holding means for accepting the desired components and discharging liquid pumped by said third pumping means in said second direction through said column.

24. Apparatus according to claim 23, wherein means are provided for preventing communication of said column with said sample receiving receptacle means when said first pumping means is pumping portions of said fluid sample in said first direction through said column and when said second pumping means is pumping auxiliary liquid in said first direction through said column.

25. Apparatus according to claim 22, further comprising sample receiving receptacle means separate from each of said holding means for accepting the desired components and discharging liquid pumped by said third pumping means in said second direction through said column.

26. Apparatus according to claim 25, wherein means are provided for preventing communication of said column with said sample receiving receptacle means when said first pumping means is pumping portions of said fluid sample in said first direction through said column and when said second pumping means is pumping auxiliary liquid in said first direction through said column.

27. Apparatus according to claim 23, further comprising a movable table, wherein said sample holding means includes a plurality of separate sample containers arranged in a row on said table, wherein said auxiliary liquid holding means includes a plurality of separate auxiliary liquid containers arranged in a row on said table adjacent said sample containers, wherein said sample receiving receptacle means includes a plurality of sample receiving containers arranged in a row on said table adjacent said auxiliary liquid containers, wherein a probe is connected to one end of said column, and wherein means are provided for selectively and sequentially communicating said probe with respective ones of said sample, auxiliary liquid, and sample receiving containers in such a manner that said probe is communicated with one of said sample containers when said first pumping means is pumping portions of said fluid sample in said first direction through said column, that said probe is communicated with one of said auxiliary liquid containers when said second pumping means is pumping auxiliary liquid in said first direction through said column, and that said probe is communicated with one of said sample receiving containers when said third pumping means is pumping the desired components and discharging liquid in said second direction through said column.

28. Apparatus according to claim 26, further comprising a movable table, wherein said sample holding means includes a plurality of separate sample containers arranged in a row on said table, wherein said auxiliary liquid holding means includes a plurality of separate auxiliary liquid containers arranged in a row on said table adjacent said sample containers, wherein said sample receiving receptacle means includes a plurality of sample receiving containers arranged in a row on sai table adjacent said auxiliary liquid containers, wherein a probe is connected to one end of said column, and wherein means are provided for selectively and sequentially communicating said probe with respective ones of said sample, auxiliary liquid, and sample receiving containers in such a manner that said probe is communicated with one of said sample containers when said first pumping means is pumping portions of said fluid sample in said first direction through said column, that said probe is communicated with one of said auxiliary liquid containers when said second pumping means is pumping auxiliary liquid in said first direction through said column, and that said probe is communicated with one of said sample receiving containers when said third pumping means is pumping the desired components and discharging liquid in said second direction through said column.

* * * * *